United States Patent [19]

Hakansson et al.

[11] Patent Number: 5,032,080
[45] Date of Patent: Jul. 16, 1991

[54] ORTHODONTIC APPLIANCE BRACKET AND ARCH

[75] Inventors: Henrik Hakansson, Rönninge; Dick Sjögren, Stockholm, both of Sweden

[73] Assignee: Scandinavian Bioortodontic AB, Sweden

[21] Appl. No.: 370,598

[22] Filed: Jun. 23, 1989

[30] Foreign Application Priority Data

Apr. 12, 1989 [SE] Sweden .................. 8901312-2
Apr. 12, 1989 [SE] Sweden .................. 8901313-0
Apr. 12, 1989 [SE] Sweden .................. 8901314-8

[51] Int. Cl.⁵ .................................. A61C 3/00
[52] U.S. Cl. ................................................ 433/8
[58] Field of Search ........................ 433/8, 9, 20

[56] References Cited

U.S. PATENT DOCUMENTS

| 3,922,787 | 12/1975 | Fischer et al. | 433/8 X |
| 4,249,897 | 2/1981 | Anderson | 433/8 |
| 4,302,532 | 11/1981 | Wallshein | 433/8 |
| 4,337,037 | 6/1982 | Kurz | 433/8 |
| 4,585,414 | 4/1986 | Kottemann | 433/20 |
| 4,659,310 | 4/1987 | Kottemann | 433/20 |
| 4,717,341 | 1/1988 | Goldberg et al. | 433/9 |
| 4,731,018 | 3/1988 | Adell | 433/20 |
| 4,820,151 | 4/1989 | Popisil | 433/8 X |
| 4,869,666 | 9/1989 | Talass | 433/20 |

Primary Examiner—Robert P. Swiatek
Assistant Examiner—Nicholas D. Lucchesi
Attorney, Agent, or Firm—Ostrolenk, Faber, Gerb & Soffen

[57] ABSTRACT

A dental appliance formed of a bracket and an arch. The bracket is adapted to be detachably secured to a patient's tooth. The bracket is formed from a material which is substantially inert to water, which has a low coefficient of friction, and which has deformation properties which enable the bracket to absorb and equalize minor displacement of the tooth without adversely affecting the original shape of the arch. The arch cooperates with the bracket when the bracket is detachably secured to the tooth of the patient. The arch includes wire or ribbon, and a relatively thin coating over the wire or ribbon. The coating is substantially tooth-colored and has a low coefficient of friction.

10 Claims, 2 Drawing Sheets

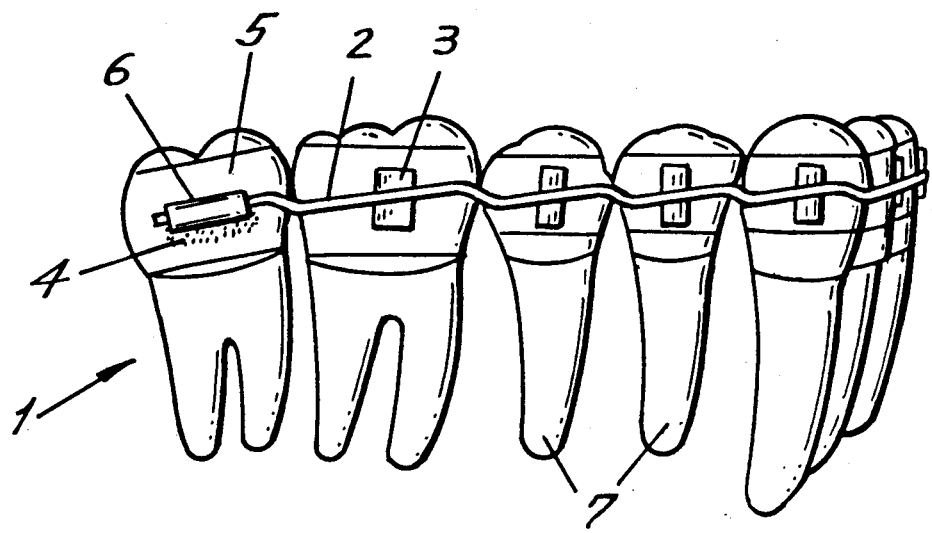
FIG. 1.
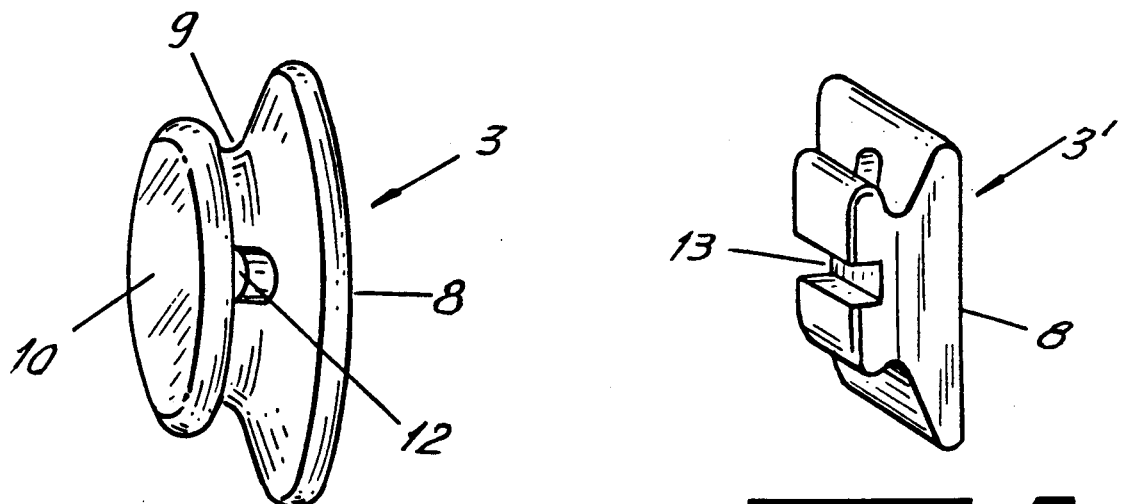
FIG. 2.
FIG. 3.
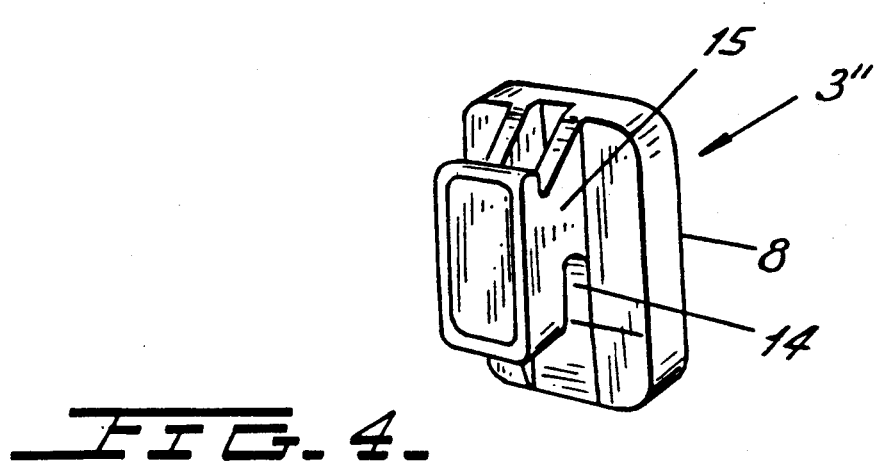
FIG. 4.

ORTHODONTIC APPLIANCE BRACKET AND ARCH

BACKGROUND OF THE INVENTION

1. Field of the Invention

The invention relates to an orthodontic appliance for use in orthodontic therapy. The orthodontic appliance includes brackets and an arch. The invention also relates to a bracket for use in an orthodontic appliance. The invention also relates to an arch for use in an orthodontic appliance.

2. Description of the Related Art

Orthodontic therapy has a long tradition, beginning with an arch designed by Pierre Fauchard in 1728.

In 1887, Edward H. Angle designed the then revolutionary "E-arch" which enabled tooth crowns to be correctly tilted. Angle realized the deficiencies in this technique and subsequently developed the "Pin and Tube" system which enabled even the roots of teeth to be correctly induced. This was the first method which required bands with special securing or anchoring members.

After that, Angle developed "The Ribbon Arch," which required brackets. These brackets were small metal plates, with dimensions of 0.036 in. (1.4 mm) and 0.022 in. (0.87 mm). Each of the plates was individually cemented to a tooth. These brackets were used for a long time. They were not modified until 1956 by Begg, the "Light Wire" technique.

Angle introduced the "Edgewise technique" in 1925 and published his findings in *The Dental Cosmos* Dec. 1928, "The Latest and Best in Orthodontic Mechanism." Angle emphasized that no other orthodontic treatment had ever been tested more thoroughly before being publicly introduced. Angle also emphasized the significance of balance in the treatment of a malocclusion.

The Edgewise technique displaces teeth in three planes with a single rectangular or quadratic arch. The edgewise arch is formed of a rectangular wire with dimensions of 0.022 in. (0.87 mm) and 0.028 in. (1.1 mm) or 0.025 in. (0.98 mm). The arch is incorporated into brackets or soldered onto ribbon cemented to the patient's teeth. A gold-platina alloy was used for the ribbon, brackets, and arches before stainless steel came into use. Loops and spurs are soldered onto the ribbon and form attachments when soldering the arch. An ideal arch is constructed at the start of treatment. If irregularities are too great, the arch is gradually modified. For serious anomalies, a round arch, with a diameter of 0.022 in. (0.87 mm), is used, or an edgewise arch with dimensions of 0.022 in. (0.87 mm).

Angle's pupils, Brodie and Strang, were responsible for the next phase in the development of the Edgewise technique. They improved the ribbons and brackets, introduced new materials, used rounder arches, and made other changes.

In 1930, Charles Tweed drew attention both to the necessity of extraction and the significance of the anchoring mechanism. Tweed also determined that an orthodontic apparatus should be able to create constant maximal resistance in the anchoring region and minimal resistance in the region in which displacement was desired.

In 1953, Steiner proposed the use of 0.018 in. (0.71 mm) slot brackets and arches of stainless steel, and found that the treatment period was reduced. Steel replaced gold during the years following and many orthodontists started using such brackets.

Efforts have been made in recent years to improve upon the prior art by making arches of thinner material, and by making other minor changes.

However, such designs have many serious drawbacks. For example, it has been established that undesirable metal ions are dissolved out of stainless materials by the constant influence of saliva.

Furthermore, the use of stainless material for the brackets produces an extremely unattractive appearance. However, repeated attempts to improve aesthetics by manufacturing brackets of bone-colored plastic materials have been unsuccessful. Such plastic materials have been too brittle and the brackets formed of such material have not been strong enough, particularly if a relatively strong metal wire is used in the arch.

To solve this problem, attempts have been made (U.S. Pat. No. 4,302,532) to reinforce the archwire slots in such plastic brackets with special coatings or liners of harder material, such as metal, to reduce wear between the steel arch and the archwire slot. This has improved the wear resistance of orthodontic appliances. However, the prior art plastic materials are still too brittle and too affected by the constant influence of saliva. Moreover, the reinforcement described in U.S. Pat. No. 4,302,532 is extremely complicated and becomes detached in practice due to friction between the archwire and the reinforcement. Moreover, such reinforced plastic brackets are expensive to manufacture and are unattractive.

It has also been proposed (U.S. Pat. No. 4,180,912) to improve the appearance of orthodontic appliances by providing conventional steel brackets with an outer casing of plastic. However, this proposal is extremely complicated and the casings are often damaged by the arch. The proposal is nonfunctional in practice.

Ceramic brackets have also been tried. However, such ceramic brackets cause wear while adhered to tooth enamel and cause surface damage when finally removed.

Therefore, stainless steel is still generally used in brackets and arches.

Finally, an orthodontic appliance which is built up on the lingual surfaces of a patient's teeth is disclosed in Sweden Patent No. 85 01 579-0. However, the patient continually encounters the various parts of such an appliance with the tip of the tongue and it is difficult to maintain an acceptable level of hygiene.

SUMMARY OF THE INVENTION

It is an object of the present invention to eliminate the above-mentioned drawbacks of the prior art and to provide brackets which are both attractive and fully functional.

A further object of the invention is to produce an arch which has the necessary permanence of shape, which can be used with plastic brackets without damaging them, and which is inconspicuous.

These objects, and others, are achieved by the invention which relates to a dental appliance, including: (a) a bracket adapted to be detachably secured to a patient's tooth, the bracket being formed from a material which is substantially inert to water, the material having a low coefficient of friction, the material having deformation properties which enable the bracket to absorb and equalize minor displacement of the tooth without adversely affecting the dental appliance; and (b) an arch for cooperating with the bracket when the bracket is detachably secured to the tooth of the patient, the arch including: (1) wire or ribbon; and (2) a thin coating over the wire or ribbon, the coating being substantially tooth-colored, the coating having a low coefficient of friction.

The invention also relates to a bracket for use within such an appliance and to an arch for use within such an appliance.

The bracket material proposed according to the invention, together with the archwire coated with plastic, offers for the first time an acceptable appearance for orthodontic appliances, making the appliances considerably less conspicuous than previous constructions. A completely unique cooperation between the dental arch material and the bracket material is obtained by a dental appliance fabricated according to the invention, when it comes to producing correction forces exerted on the teeth. Thanks to the deformation properties of the plastic material proposed according to the invention, the same dental arch can be used, for instance, for a considerably longer period of time than before and friction forces arising between archwire and plastic brackets can be controlled far more efficiently than before.

The material enables the fabrication of brackets which can easily be secured to tooth enamel without the enamel being damaged upon removal of the brackets. Furthermore, the bracket material exhibits such deformation properties that even after repeated varying deformation the material is able to resume its original shape to at least 70%. This is of great significance if the teeth are to be allowed a certain freedom of movement in relation to the arch. Finally, the bracket material has a suitable coefficient of friction for cooperation with the plastic-coated, less visible, archwire.

Other features and objects of the present invention will become apparent from the following detailed description of the preferred embodiments of the invention considered in conjunction with the accompanying drawings.

BRIEF DESCRIPTION OF THE DRAWINGS

FIG. 1 is a side view of an orthodontic appliance in use on a row of teeth;

FIG. 2 is a perspective view of a bracket;

FIG. 3 is a perspective view of another bracket;

FIG. 4 is a perspective view of still another bracket;

DETAILED DESCRIPTION OF THE PREFERRED EMBODIMENTS

Figure 5:
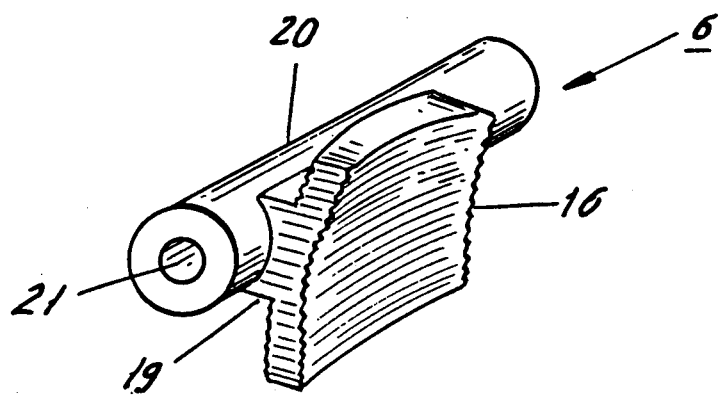
FIG. 5 is a perspective view of a molar sleeve.

FIG. 1 illustrates a row 1 of teeth 7 within an upper jaw, a dental arch 2, and individual brackets 3. The brackets 3 are detachably secured by cement or the like (not illustrated) to each tooth 7. One of the brackets 3 is designed as a molar sleeve 6. One end 4 of the arch 2 is detachably secured to the molar sleeve 6 which, in turn, is secured to a molar 5. The other end (not illustrated) of the arch 2 is similarly detachably secured to a similar molar sleeve (not illustrated). The arch 2 is fabricated individually by an orthodontist for each patient to be treated.

The brackets 3 (including the molar sleeve 6) are injection molded from an inconspicuous, preferably bone or tooth-colored, material which has good elasticity, high tensile strength, and high notch impact strength. A preferred thermoplastic material is an unreinforced polysulfone plastic marketed by Amoco Performance Products, Inc. under the tradename UDELL, designation P 1700. This material is produced by a nucleophillic substitution reaction between the di-sodium salt of bisphenol A and 4.4-dichloro-diphenyl sulfone. The material has the following chemical structure:

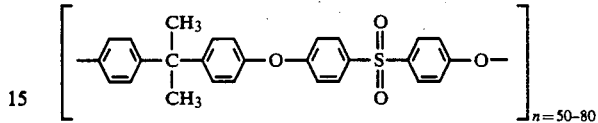

The most important part of the polysulfone is the diphenyl sulfone group:

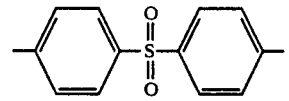

Ether and isopropylidene are connected to the diphenyl sulfone group to give the material good elasticity at high strength. The material is able to resume at least 70% of its original shape after repeated deformation. The unreinforced thermoplastic material has a tensile strength of 50–90 N/mm$^2$, preferably 70 N/mm$^2$; a modulus of elasticity of 2001–2600 N/mm$^2$, preferably 2480 N/mm$^2$; and a notch impact strength of 40–80 J/n at a thickness of 2.8–15.0 mm, preferably an impact strength of 420 kJ/mm$^2$; and a coefficient of friction of 0.65.

The preferred material is also inert. In particular, the polysulfone thermoplastic is inert to water so that water from saliva is not absorbed. Such absorption has been a serious problem with plastic brackets made of acrylate plastics, which readily absorb water.

Moreover, the preferred material can be easily secured to the enamel of the teeth 7 and does not damage the enamel when removed.

As illustrated in FIG. 1, the dental arch 2 contacts but is not permanently connected to the brackets 3. To achieve controlled abutment, each bracket 3 has an archwire slot as illustrated more clearly in FIGS. 2–4.

The bracket 3 illustrated in FIG. 2 is designed to be secured to the enamel of the tooth 7 by a rear base plate 8. An intermediate flange 9 protrudes from the base plate 8 and is integral with a circular front plate 10. An opening 12 for use as an archwire slot extends through the intermediate flange 9. Alternatively, the dental arch 2 may be placed in the space between the base plate 8 and the front plate 10 above or below the flange 9.

The bracket 3' illustrated in FIG. 3 includes a transverse recess 13 for use as an archwire slot. The recess 13 is located in front of the bracket 3'.

The bracket 3" illustrated in FIG. 4 includes a transverse recess 14 located between the base plate 8 and a central holder 15 protruding from the base plate 8.

Referring to FIG. 5, the molar sleeve 6 includes a base plate 16 adapted to be detachably cemented to the molar 5. A transverse flange 19 protrudes from the plate 16 and is attached to a tubular member 20. The tubular member 20 has a through-hole 21. The molar sleeve 6 secures the end 4 of the dental arch 2. That is, the end 4 is inserted through the through-hole 21 and then suitably bent into a secured position.

Metal ions cannot be dissolved out of the molar sleeve 6 by saliva, as was possible with the prior art metal sleeves.

Figure 6:
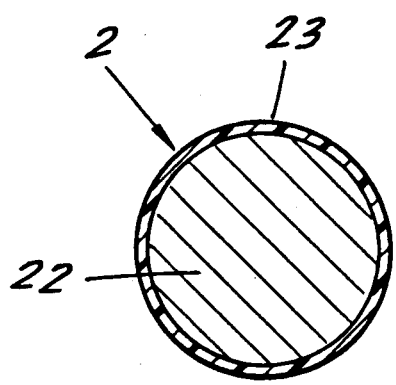
FIG. 6 is a cross-sectional view of a dental arch.
Figure 7:
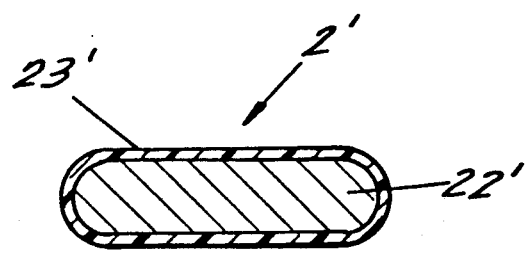
FIG. 7 is a cross-sectional view of another dental arch.

FIGS. 6-7 are sectional views through the arch 2. In FIG. 6, the arch 2 is in the form of a wire 2 with a circular cross-section. The wire 2 has a core 22. It is important that the arch 2 retain its shape in use. Accordingly, the core 22 is fabricated from cold-drawn (or cold tempered) steel wire with a diameter of 0.018 in. (0.71 mm). The core 22 is subjected to a brief heat treatment. The steel core 22 is then carefully cleaned and coated with a layer of bone or tooth-colored polyamide 6/6 23 to a thickness of about 0.02-0.2 mm, preferably about 0.05-0.1 mm, preferably about 0.05 mm. The polyamide coating 23 has a coefficient of friction of 0.8.

In FIG. 7, the arch 2 is in the form of a ribbon 2 with a core 22' and a coating 23'.

The invention is not limited to the polyamide coating described. Other plastic materials may be used, particularly those having low coefficients of friction.

The design of the dental appliance permits relative movement between the arch 2 and the brackets 3. Since the arch 2 and the brackets 3 are formed of materials with low coefficients of friction, they do not damage each other during such movement. Further, the brackets 3 are themselves sufficiently elastic to absorb forces caused by displacement of the teeth 7 during the correction process such that the original shape of the arch 2 is not affected.

Practical experiments using dental appliances according to the invention have shown that, in many cases, the arch has only had to be changed twice during the entire period of treatment (normally about 20 months). One arch can be used for up to six months. This is a great step forward from the prior art.

Although the invention has been described and illustrated in detail, it is clearly understood that the same is by way of illustration and example only and is not to be taken by way of limitation. The spirit and scope of the invention should be limited only by the appended claims.

What is claimed is:

1. A bracket for use within a dental appliance, said bracket being adapted to be detachably secured to a patient's tooth, said bracket being formed from a material which is substantially inert to water, said material having a low coefficient of friction, said material having deformation properties which enable said bracket to absorb and equalize minor displacement of the tooth without adversely affecting the dental appliance;
wherein said material is a thermoplastic material, said thermoplastic material resuming at least 70% of its original shape after repeated deformation, said thermoplastic material having a tensile strength of 50-90 N/mm$^2$, a modulus of elasticity of 2001-2600 N/mm$^2$, and a notch impact strength of 40-80 J/n at a thickness of 2.8-15.0 mm;
wherein said material contains diphenyl sulfone groups having the formula:

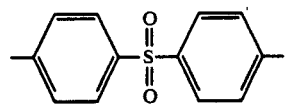

and
wherein said bracket is formed essentially entirely of said thermoplastic material.

2. The bracket of claim 1, wherein said bracket is a molar sleeve.

3. A dental appliance, comprising:
(a) a bracket adapted to be detachably secured to a patient's tooth, said bracket being formed from a thermoplastic material which is substantially inert to water, said material having a low coefficient of friction, said material having deformation properties which enable said bracket to absorb and equalize minor displacement of the tooth without adversely affecting said dental appliance, wherein said thermoplastic material contains diphenylsulfone groups having the formula:

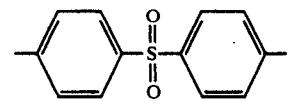

and
(b) an arch for cooperating with said bracket when said bracket is detachably secured to the tooth of the patient, said arch comprising:
(1) wire or ribbon; and
(2) a thin polyamide coating over said wire or ribbon, said coating being substantially tooth-colored, said coating having a low coefficient of friction.

4. The dental appliance of claim 3, wherein said thermoplastic material of said bracket resumes at least 70% of its original shape after repeated deformation.

5. The dental appliance of claim 4, wherein said thermoplastic material has a tensile strength of 50-90 N/mm$^2$, a modulus of elasticity of 2001-2600 N/mm$^2$, and a notch impact strength of 40-80 J/n at a thickness of 2.8-15.0 mm.

6. The dental appliance of claim 3, wherein said wire or ribbon of said arch includes cold-drawn steel.

7. The dental appliance of claim 3, wherein said coating has a thickness of 0.02-0.2 mm.

8. The dental appliance of claim 7, wherein said coating has a thickness of 0.05-0.1 mm.

9. The dental appliance of claim 3, wherein said bracket includes a slot for cooperating with said arch.

10. A method of use, comprising:
providing brackets formed of an unreinforced thermoplastic material containing diphenyl sulfone groups; and
using said brackets in cooperation with a dental arch to fabricate a dental appliance for orthodontic therapy.

* * * * *